US012706216B2

(12) United States Patent
Shute et al.

(10) Patent No.: US 12,706,216 B2
(45) Date of Patent: Aug. 11, 2026

(54) PHENOTYPE-SPECIFIC HEART FAILURE DIAGNOSIS AND MANAGEMENT

(71) Applicant: Cardiac Pacemakers, Inc., St. Paul, MN (US)

(72) Inventors: Jonathan Bennett Shute, Eagan, MN (US); Bin Mi, Arden Hills, MN (US); Pramodsingh Hirasingh Thakur, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 3 days.

(21) Appl. No.: 18/631,491

(22) Filed: Apr. 10, 2024

(65) Prior Publication Data

US 2024/0347199 A1 Oct. 17, 2024

Related U.S. Application Data

(60) Provisional application No. 63/458,482, filed on Apr. 11, 2023.

(51) Int. Cl.
*G16H 50/20* (2018.01)
*G16H 40/67* (2018.01)

(52) U.S. Cl.
CPC ............. *G16H 50/20* (2018.01); *G16H 40/67* (2018.01)

(58) Field of Classification Search
CPC ........ G16H 50/20; G16H 40/67; G16H 50/70; G16H 20/30
USPC ........................................................... 705/2–3
See application file for complete search history.

(56) References Cited

U.S. PATENT DOCUMENTS

| | | | | |
|---|---|---|---|---|
| 12,220,212 | B2 * | 2/2025 | Zile | A61N 1/39622 |
| 2017/0095160 | A1 * | 4/2017 | Thakur | A61B 5/0535 |
| 2018/0153416 | A1 * | 6/2018 | Zile | A61B 5/7264 |
| 2021/0236053 | A1 * | 8/2021 | Narayan | A61B 5/363 |

FOREIGN PATENT DOCUMENTS

| | | | | |
|---|---|---|---|---|
| EP | 4166088 | A1 * | 4/2023 | A61B 8/5223 |
| WO | WO-2019212833 | A1 * | 11/2019 | G16H 50/70 |

OTHER PUBLICATIONS

Shah et al., "Phenotype-Specific Treatment of Health Failure With Preserved Ejection Fraction, A Multiorgan Roadmap", Circulation, 2016; 134:73-90, DOI: 10.1161/CIRCULATIONAHA.116.021884 Jul. 5, 2016 (Year: 2016).*

(Continued)

*Primary Examiner* — Joy Chng
(74) *Attorney, Agent, or Firm* — Nelson Mullins Riley & Scarborough LLP

(57) ABSTRACT

Systems and methods for monitoring heart failure status in a patient are discussed. A medical-device system receives physiological and clinical information of the patient, and classifies the patient into one of a plurality of phenotypes using the received information. The plurality of phenotypes each can be characterized by a cluster physiological, clinical, demographic, or comorbidity features in a multi-dimensional feature space. Based on the classified phenotype, a heart failure detector determines a heart failure detection setting for the patient, and detects a heart failure status in the patient using the heart failure detection setting. A therapy circuit can deliver or adjust a heart failure therapy in response to the detected heart failure status.

20 Claims, 6 Drawing Sheets

(56) References Cited

OTHER PUBLICATIONS

Chirinos, Julio A., et al., "Arterial Wave Reflections and Incident Cardiovascular Events and Heart Failure: The Multiethnic Study of Atherosclerosis", J Am Coll Cardiol. Nov. 20, 2012; 60(21): 2170-2177. doi:10.1016/j.jacc.2012.07.054.

Shah, Amil M., et al., "Cardiac Structure and Function in Heart Failure With Preserved Ejection Fraction, Baseline Findings From the Echocardiographic Study of the Treatment of Preserved Cardiac Function Heart Failure With an Aldosterone Antagonist Trial", CIRCHEARTFAILURE.113.000887 Downloaded from http://ahajournals.org by on Apr. 10, 2024.

Shah, Sanjiv J., et al., "Phenotype-Specific Treatment of Heart Failure With Preserved Ejection Fraction, A Multiorgan Roadmap", Circulation. 2016;134:73-90. DOI: 10.1161/CIRCULATIONAHA.116.021884 Jul. 5, 2016.

Shah, Sanjiv J., et al., "Physiology of the Third Heart Sound: Novel Insights from Tissue Doppler Imaging", Journal of the American Society of Echocardiography vol. 21 No. 4, Apr. 2008, pp. 394-400.

* cited by examiner

PHENOTYPE-SPECIFIC HEART FAILURE DIAGNOSIS AND MANAGEMENT

CLAIM OF PRIORITY

This application claims the benefit of U.S. Provisional Application No. 63/458,482 filed on Apr. 11, 2023, which is hereby incorporated by reference in its entirety.

TECHNICAL FIELD

This document relates generally to medical devices, and more particularly, to systems, devices and methods for detecting and managing heart failure.

BACKGROUND

Congestive heart failure (CHF) is a leading cause of death in the United States and globally. CHF is the loss of pumping power of the heart, and may affect left heart, right heart, or both sides of the heart, and result in the inability to deliver enough blood to meet the demands of peripheral tissues. CHF patients typically have enlarged heart with weakened cardiac muscles, resulting in reduced contractility and poor cardiac output of blood. CHF may be treated by drug therapy, or by an implantable medical device (IMD) such as for providing electrostimulation therapy. Although usually a chronic condition, CHF may occur suddenly.

Heart failure with preserved ejection fraction (HFpEF) and heart failure with reduced ejection fraction (HFrEF) are two major types of heart failures related to ejection fraction (EF). HFpEF, also known as diastolic heart failure, accounts for more than 50% of clinical heart failure cases. HFpEF occurs due to insufficient filling of the left ventricle with blood. The ventricle does not relax properly and thus is unable to fill with blood properly during the diastole, such as due to stiff and or thickened left ventricular (LV) heart muscles. However, patients with HFpEF generally have normal or near normal EF (e.g., greater than 50%). Coronary artery disease, high blood pressure, aortic stenosis, hypertrophic cardiomyopathy and pericardial disease are major causes of HFpEF. HFrEF, also known as systolic heart failure, occurs when the left ventricle fails to pump an adequate amount of oxygen-rich blood to the body, resulting a lower than normal EF (e.g., less than 40%). Heart attacks, coronary artery disease, high blood pressure, mitral regurgitation, viral myocarditis and aortic stenosis are some major cause of HFrEF.

Some IMDs are capable of monitoring CHF patients and detect events leading to worsening heart failure (WHF). These IMDs may include sensors to sense physiological signals from a patient. Frequent patient monitoring may help reduce heart failure hospitalization. Identification of patient at an elevated risk of developing WHF, such as heart failure decompensation, may help ensure timely treatment and improve prognosis and patient outcome. Identifying and safely managing the patients at elevated risk of WHF may avoid unnecessary medical interventions, hospitalization, and thereby reduce healthcare cost.

An IMD may contain electronic circuitry, such as a pulse generator, to generate and deliver electrostimulation to excitable tissues or organs, such as a heart. The electrostimulation may help restore or improve a CHF patient's cardiac performance, or rectify cardiac arrhythmias. One example of such electrostimulation therapy is resynchronization therapy (CRT) for correcting cardiac dyssynchrony in CHF patients.

SUMMARY

Frequent monitoring of CHF patients and timely detection of intrathoracic fluid accumulation or other events indicative of heart failure decompensation status may help prevent WHF in CHF patients, hence reducing cost associated with heart failure hospitalization.

Ambulatory medical devices for monitoring heart failure patient may include implantable medical devices (IMD), subcutaneous medical devices, wearable medical devices or other external medical devices. An ambulatory medical device may be coupled to one or more physiological sensors to sense electrical activity and mechanical function of the heart. The ambulatory medical device may optionally deliver therapy, such as electrical stimulation pulses, to the patient to restore or improve patient cardiac function. Some of these devices may provide diagnostic features, such as using transthoracic impedance or other sensor signals. For example, fluid accumulation in the lungs decreases the transthoracic impedance due to the lower resistivity of the fluid than air in the lungs. The fluid accumulation may also elevate ventricular filling pressure, resulting in a louder S3 heart sound. Additionally, fluid accumulation in the lungs may irritate the pulmonary system and leads to decrease in tidal volume and increase in respiratory rate.

Identification of patient at an elevated risk of WHF may help ensure timely intervention such as device therapy or drug therapy, thereby improving the prognosis and patient outcome. On the other hand, identifying and safely managing patients with low risk of WHF may avoid unnecessary medical interventions, thereby reducing healthcare cost. Desired performance of WHF risk stratification may include one or more of a high sensitivity, a high specificity, a high positive predictive value (PPV), or a negative predictive value (NPV). The sensitivity represents an accuracy of identifying patients with relatively a high risk of WHF. The specificity represents an accuracy of identifying patients with relatively a low risk of WHF.

Echocardiography and biomarker tests (e.g., natriuretic peptide tests) are standard approaches to diagnose heart failure. The ratio of early diastolic mitral inflow velocity to early diastolic mitral annulus velocity (also known as E/e' ratio), estimated using tissue Doppler echocardiography, has been used to evaluate the left ventricular (LV) filling pressure and LV stiffness, and to diagnose heart failure such as HFpEF. B-type natriuretic peptide (BNP) or N-terminal-pro-BNP (NT-pro-BNP)) is a protein secreted from heart muscles during hemodynamic overload, and can reflect LV end-diastolic wall stress, and has been used as a marker for the evaluation of HFpEF and assessment of prognosis. Clinically, HFpEF may also be diagnosed using cardiac catheterization during exertion (e.g., exercise or other activities) to detect an exaggerated increase in LV filling pressure from baseline at rest, a hallmark signature of HFpEF.

Although these conventional echocardiography and/or biomarker tests are generally effective in diagnosing HFrEF, they can be more challenging to produce consistent and reliable diagnosis of HFpEF. For example, some patients with invasively proven HFpEF nevertheless displayed normal NT-pro-BNP levels. The E/e' ratio used as a surrogate for filling pressure, although a good indicator of large pressure differences, may not be a reliable indicator of smaller changes in filling pressure (e.g., changes with exercise). Cardiac catheterization during exertion (to detect an increase in LV filling pressure) can be difficult to deploy as a screening tool in a clinical setting. Furthermore, HFpEF can be clinically complicated with a variety of pathophysiological presentations other than diastolic dysfunction including, for example, longitudinal systolic dysfunction, chronotropic incompetence, autonomic dysfunction, endothelial dysfunction, pulmonary hypertension, abnormal atrioventricular coupling, skeletal muscle abnormalities, information, arterial stiffness, extra-cardiac causes of volume overload, among others. As such, HFpEF patients can be underdiagnosed or misdiagnosed, and do not get properly recognized until they have had multiple episodes of acute decompensated heart failure (ADHF) with new or worsening signs and symptoms leading to hospitalization or an emergency department visit. For at least the above reasons, the present inventors have recognized that there remains a considerable need of systems and methods for diagnosing CHF, particularly HFpEF, and managing patients with such conditions.

This document discusses, among other things, a patient management system for detecting and managing heart failure in a patient. In accordance with one embodiment, a medical-device system can receive physiological and clinical information of the patient, and classify the patient into one of a plurality of phenotypes using the received physiological and clinical information. The plurality of phenotypes each can be characterized by a cluster of features (e.g., physiological, clinical, demographic, or comorbidity features, among others) in a multi-dimensional feature space. Based on the classified phenotype, a heart failure detector included in the system can determine a heart failure detection setting for the patient, and detect a heart failure status in the patient using the determined heart failure detection setting. The system may include a therapy circuit to deliver or adjust a heart failure therapy in response to the detected heart failure status.

Example 1 is a medical-device system for detecting and managing heart failure in a patient, the medical-device system comprising: a receiver circuit configured to receive physiological and clinical information of the patient; and a heart failure detector circuit configured to: classify the patient into one of a plurality of phenotypes using the received physiological and clinical information; determine a heart failure detection setting based on the classified phenotype of the patient; and detect a heart failure status in the patient using the received physiological and clinical information and the determined heart failure detection setting.

In Example 2, the subject matter of Example 1 optionally includes, wherein the receive physiological and clinical information includes heart sound information, wherein the heart failure detector circuit is configured to detect the heart failure status including a presence or absence of a heart failure with preserved ejection fraction (HFpEF) using the heart sound information and the determined heart failure detection setting.

In Example 3, the subject matter of any one or more of Examples 1-2 optionally include, wherein the plurality of phenotypes are each characterized by a cluster of physiological and clinical features in a multi-dimensional feature space including at least one of: demographic feature; clinical or laboratory test data feature; medical history data; medication information; or heart failure comorbidity information.

In Example 4, the subject matter of Example 3 optionally includes, wherein the cluster of physiological and clinical features characterizing one or more of the plurality of phenotypes further include sensor signal features produced by one or more ambulatory physiological sensors.

In Example 5, the subject matter of any one or more of Examples 1-4 optionally include, wherein the heart failure detector is configured to classify the patient into one of the plurality of phenotypes using a trained machine learning (ML) or artificial intelligence model.

In Example 6, the subject matter of any one or more of Examples 1-5 optionally include, wherein the heart failure detector is configured to classify the patient into one of the plurality of phenotypes based on a similarity between the received physiological and clinical information of the patient and one or more of the plurality of phenotypes.

In Example 7, the subject matter of any one or more of Examples 1-6 optionally include, wherein the heart failure detector is further configured to: receive information sensed from the patient by at least one phenotype-specific sensor for the classified phenotype; and confirm or modify the classified phenotype of the patient using the received information sensed by the at least one phenotype-specific sensor.

In Example 8, the subject matter of any one or more of Examples 1-7 optionally include a storage device configured to store a correspondence between the plurality of phenotypes and corresponding candidate heart failure detection settings, wherein to determine the heart failure detection, the heart failure detector circuit is configured to select from the stored candidate heart failure detection settings based on the classified phenotype.

In Example 9, the subject matter of any one or more of Examples 1-8 optionally include a sensor circuit configured to selectively sense physiological signal based on the classified phenotype, wherein the heart failure detector circuit is configured to detect the heart failure status using the selectively sensed physiologic signal.

In Example 10, the subject matter of any one or more of Examples 1-9 optionally include, wherein to detect the heart failure status in the patient, the heart failure detector circuit is configured to: compute a composite signal index using the received physiological and clinical information and the determined heart failure detection setting; and detect the heart failure status in response to the composite signal index satisfying a specific condition.

In Example 11, the subject matter of Example 10 optionally includes, wherein the heart failure detector circuit is configured to determine or adjust a threshold value based on the classified phenotype, and to detect the heart failure status based on a comparison between the composite signal index and the determined or adjusted threshold value.

In Example 12, the subject matter of any one or more of Examples 10-11 optionally include, wherein the heart failure detector circuit is configured to: determine or adjust weights for one or more of a plurality of signal metrics derived from the received physiological and clinical information; and compute the composite signal index using a weighted combination of the plurality of signal metrics.

In Example 13, the subject matter of Example 12 optionally includes, wherein the heart failure detector circuit is configured to determine or adjust the weights for the one or more of the plurality of signal metrics further based on a severity of a symptom or a comorbid condition associated with the classified phenotype.

In Example 14, the subject matter of Example 13 optionally includes, wherein the classified phenotype is a diastolic dysfunction phenotype, wherein the plurality of signal metrics include an S3 intensity metric, wherein the heart failure detector circuit is configured to: determine or adjust the weights for the one or more of the plurality of signal metrics including to reduce a weight for the S3 intensity metric if the patient has normal or mild diastolic dysfunction, and increase the weight for the S3 intensity metric if the patient has moderate or severe diastolic function; and compute the composite signal index using a weighted combination of the plurality of signal metrics including the S3 intensity metric.

In Example 15, the subject matter of any one or more of Examples 1-14 optionally include a therapy circuit configured to generate and deliver a heart failure therapy to the patient in accordance with the detected heart failure status.

Example 16 is a method of detecting and managing heart failure in a patient using a medical-device system, the method comprising: receiving physiological and clinical information of the patient; classifying the patient into one of a plurality of phenotypes using the received physiological and clinical information; determining a heart failure detection setting based on the classified phenotype of the patient; and detecting a heart failure status in the patient using the received physiological and clinical information and the determined heart failure detection setting.

In Example 17, the subject matter of Example 16 optionally includes, wherein the plurality of phenotypes are each characterized by a cluster of physiological and clinical features in a multi-dimensional feature space including at least one of: demographic feature; clinical or laboratory test data feature; medical history data; medication information; heart failure comorbidity information; or sensor signal features produced by one or more ambulatory physiological sensors.

In Example 18, the subject matter of any one or more of Examples 16-17 optionally include, wherein classifying the patient into one of the plurality of phenotypes includes using a trained machine learning (ML) or artificial intelligence model.

In Example 19, the subject matter of any one or more of Examples 16-18 optionally include, wherein classifying the patient into one of the plurality of phenotypes is based on a similarity between the received physiological and clinical information of the patient and one or more of the plurality of phenotypes.

In Example 20, the subject matter of any one or more of Examples 16-19 optionally include, further comprising: receiving information sensed from the patient by at least one phenotype-specific sensor for the classified phenotype; and confirming or modifying the classified phenotype of the patient using the received information sensed by the at least one phenotype-specific sensor.

In Example 21, the subject matter of any one or more of Examples 16-20 optionally include storing a correspondence between the plurality of phenotypes and corresponding candidate heart failure detection settings, wherein determining the heart failure detection includes selecting from the stored candidate heart failure detection settings based on the classified phenotype.

In Example 22, the subject matter of any one or more of Examples 16-21 optionally include, wherein detecting the heart failure status in the patient includes: computing a composite signal index using a weighted combination of a plurality of signal metrics derived from the received physiological and clinical information and each scaled by an adjustable weight; and detecting the heart failure status in response to the composite signal index satisfying a specific condition.

Various embodiments described herein may help improve the medical technology of device-based heart failure patient management, particularly computerized diagnosis of HFpEF. It has been recognized that patients with different heart failure phenotypes (such as characterized by respective clusters in a multi-dimensional feature spacing comprising clinical data, laboratory test results, medical history, medication, demographic information, heart failure comorbid conditions, physiological sensor data, etc.) may exhibit different clinical presentations and/or physiological reactions to the progression of heart failure. The phenotype-specific heart failure detection as discussed in this document can automatically adjust detection algorithms or detection parameters based on the patient heart failure phenotype. The patient may be classified into one of predetermined clusters each characterized by a known phenotype. When the patient medical condition changes, the patient may be reclassified into a different phenotype. The heart failure detection algorithm may be automatically adjusted to adapt to the new phenotype. In contrast to conventional heart failure detection settings invariably applied to patients with distinct physiological or clinical conditions, the present phenotype-specific heart failure detection automates the process of dynamically adjusting the detection algorithm based on patient changing medical conditions, thereby reducing the false positive rate and improving the WHF detection accuracy. The improved heart failure diagnosis can be achieved at little to no additional cost. Such improvement in heart failure patient management may reduce hospitalization and healthcare costs associated with patient management. The systems, devices, and methods discussed in this document may also allow for more efficient device memory usage, such as by storing patient phenotype that is clinically more relevant to heart failure diagnostics. As fewer false positive detections are provided, device battery life may be extended, and fewer unnecessary drugs and procedures may be scheduled, prescribed, or provided. Therapy titration, such as electrostimulation parameter adjustment, based on the detected heart failure status may not only improve therapy efficacy and patient outcome, but may also save device power. As such, overall system cost savings may be realized.

Although the discussion in this document focuses on heart failure diagnosis, this is meant only by way of example and not limitation. It is within the contemplation of the inventors, and within the scope of this document, that the systems, devices, and methods discussed herein may also be used to detect, and alert occurrence of, cardiac arrhythmias, syncope, respiratory disease, or renal dysfunctions, among other medical conditions. Additionally, although systems and methods are described as being operated or exercised by clinicians, the entire discussion herein applies equally to organizations, including hospitals, clinics, and laboratories, and other individuals or interests, such as researchers, scientists, universities, and governmental agencies, seeking access to the patient data.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting and managing heart failure in a patient. A medical-device system can receive patient physiological and clinical information of the patient, and use such information to classify the patient into one of a plurality of phenotypes. The plurality of phenotypes each can be characterized by a cluster of physiological, clinical, demographic, or comorbid features in a multi-dimensional feature space. Based on the classified phenotype, a heart failure detector can determine a heart failure detection setting for the patient, and detect a heart failure status (e.g. a HFpEF status) in the patient using the determined detection setting. A therapy circuit to deliver or adjust a heart failure therapy in response to the detected heart failure status.

Figure 1:
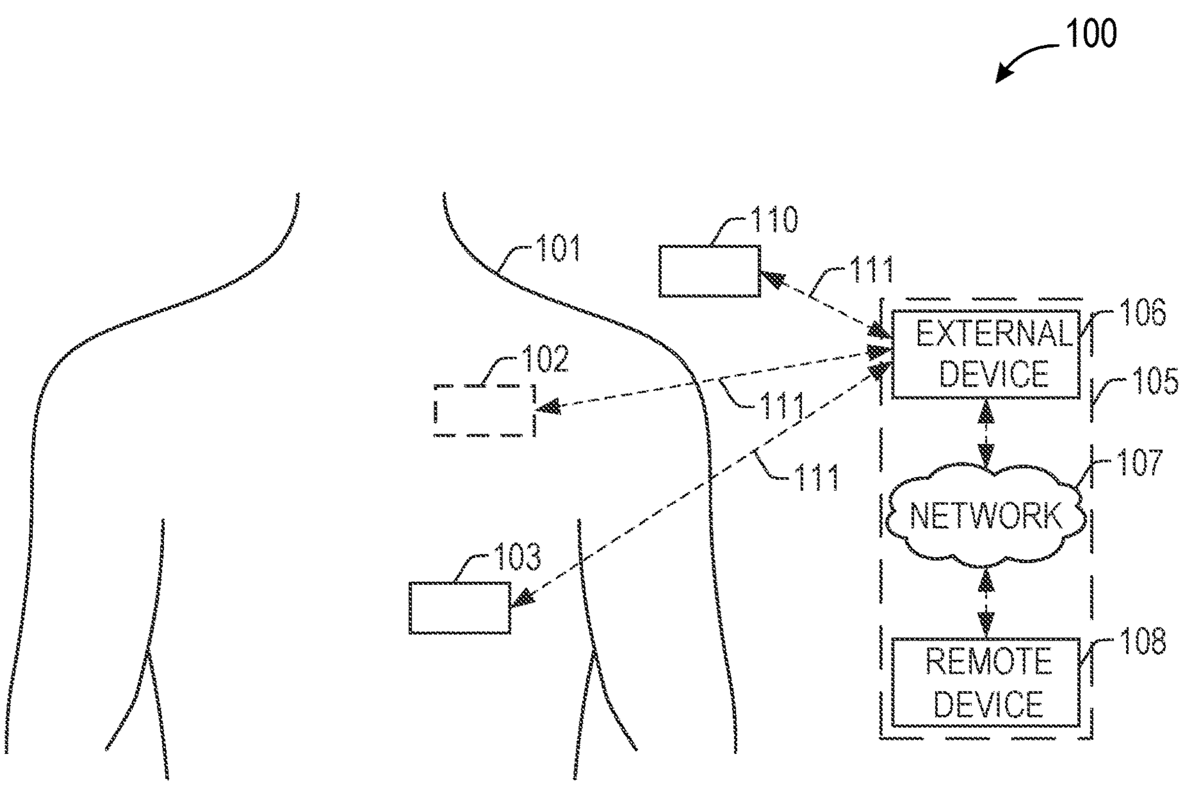
FIG. 1 illustrates generally an example of a patient monitor system and portions of an environment in which the system may operate.

FIG. 1 illustrates generally an example patient management system 100 and portions of an environment in which the patient management system 100 may operate. The patient management system 100 can perform a range of activities, including remote patient monitoring and diagnosis of a disease condition. Such activities can be performed proximal to a patient 101, such as in a patient home or office, through a centralized server, such as in a hospital, clinic, or physician office, or through a remote workstation, such as a secure wireless mobile computing device.

The patient management system 100 may include one or more ambulatory medical devices, an external system 105, and a communication link 111 providing for communication between the one or more ambulatory medical devices and the external system 105. The one or more ambulatory medical devices may include an implantable medical device (IMD) 102, a wearable medical device (WMD) 103, or one or more other implantable, leadless, subcutaneous, external, wearable, or ambulatory medical devices configured to monitor, sense, or detect information from, determine physiological information about, or provide one or more therapies to treat various conditions of the patient 101, such as one or more cardiac or non-cardiac conditions (e.g., dehydration, sleep disordered breathing, etc.).

In an example, the IMD 102 may include one or more traditional cardiac rhythm management devices implanted in a chest of a patient, having a lead system including one or more transvenous, subcutaneous, or non-invasive leads or catheters to position one or more electrodes or other sensors (e.g., a heart sound sensor) in, on, or about a heart or one or more other position in a thorax, abdomen, or neck of the patient 101. In another example, the IMD 102 may include a monitor implanted, for example, subcutaneously in the chest of patient 101, the IMD 102 including a housing containing circuitry and, in certain examples, one or more sensors, such as a temperature sensor, etc.

The IMD 102 may include an assessment circuit configured to analyze specific physiological information of the patient 101, or to determine one or more conditions or provide information or an alert to a user, such as the patient 101 (e.g., a patient), a clinician, or one or more other caregivers or processes. In an example, the IMD 102 can be an implantable cardiac monitor (ICM) configured to collected cardiac information, optionally along with other physiological information, from the patient. The IMD 102 can alternatively or additionally be configured as a therapeutic device configured to treat one or more medical conditions of the patient 101. The therapy can be delivered to the patient 101 via the lead system and associated electrodes or using one or more other delivery mechanisms. The therapy may include delivery of one or more drugs to the patient 101, such as using the IMD 102 or one or more of the other ambulatory medical devices, etc. In some examples, therapy may include cardiac resynchronization therapy for rectifying dyssynchrony and improving cardiac function in heart failure patients. In other examples, the IMD 102 may include a drug delivery system, such as a drug infusion pump to deliver drugs to the patient for managing arrhythmias or complications from arrhythmias, hypertension, or one or more other physiological conditions. In other examples, the IMD 102 may include one or more electrodes configured to stimulate the nervous system of the patient or to provide stimulation to the muscles of the patient airway, etc.

The WMD 103 may include one or more wearable or external medical sensors or devices (e.g., automatic external defibrillators (AEDs), Holter monitors, patch-based devices, smart watches, smart accessories, wrist- or finger-worn medical devices, such as a finger-based photoplethysmography sensor, etc.).

In an example, the IMD 102 or the WMD 103 may include or be coupled to an implantable or wearable sensor to sense a heart sound signal, and include a heart sound recognition circuit to recognize one or more heart sound components such as S1, S2, S3, or S4. Also included in the IMD 102 or the WMD 103 is a heart sound-based event detector circuit that can detect a physiological event (e.g., a cardiac arrhythmia episode, or a heart failure event such as HFpEF event) based at least on a heart sound metric of the detected one or more heart sound component. Examples of such heart sound metric may include an amplitude, or timing of the heart sound component within a cardiac cycle relative to a fiducial point. In some examples, at least a portion of the heart sound recognition circuit and/or the heart sound-based event detector circuit may be implemented in and executed by the external system 105.

In some examples, the IMD 102 or the WMD 103 can detect and manage heart failure in the patient 101. The IMD 102 or the WMD 103 can classify the patient 101 into one of a plurality of phenotypes using physiological and clinical information of the patient 101. The physiological information may be sensed using one or more ambulatory sensors included in or otherwise communicated with the IMD 102 or the WMD 103. The clinical information may include, for example, demographics (e.g., age and gender), diagnostic history, medications, clinical and laboratory test results, vital signs, HF comorbidities, among others. A heart failure phenotype can be characterized by a group of patient attributes related to heart failure, which may include patient vital signs, multi-dimensional patient demographic information, medical history, dietary and physical activity patterns, weight, and heart failure comorbid conditions, clinical and lab assessments, patient medication information, physiological sensor signals recorded by implantable or wearable sensors or signal metrics derived from said sensor signals, among others. The heart failure phenotype may vary from patient to patient. A patient's heart failure phenotype may also vary over time such as due to changes in patient medical condition. The plurality of heart failure phenotypes may each be associated with a corresponding detection setting. The heart failure detector circuit can determine a heart failure detection setting for the patient based on the classified phenotype, and detect a heart failure status (e.g., a HFpEF status) in the patient using the determined heart failure detection setting.

The external system 105 may include a dedicated hardware/software system, such as a programmer, a remote server-based patient management system, or alternatively a system defined predominantly by software running on a standard personal computer. The external system 105 can manage the patient 101 through the IMD 102 or one or more other ambulatory medical devices connected to the external system 105 via a communication link 111. In other examples, the IMD 102 can be connected to the WMD 103, or the WMD 103 can be connected to the external system 105, via the communication link 111. This may include, for example, programming the IMD 102 to perform one or more of acquiring physiological data, performing at least one self-diagnostic test (such as for a device operational status), analyzing the physiological data, or optionally delivering or adjusting a therapy for the patient 101. Additionally, the external system 105 can send information to, or receive information from, the IMD 102 or the WMD 103 via the communication link 111. Examples of the information may include real-time or stored physiological data from the patient 101, diagnostic data, such as detection of patient hydration status, hospitalizations, responses to therapies delivered to the patient 101, or device operational status of the IMD 102 or the WMD 103 (e.g., battery status, lead impedance, etc.). The communication link 111 can be an inductive telemetry link, a capacitive telemetry link, or a radio-frequency (RF) telemetry link, or wireless telemetry based on, for example, "strong" Bluetooth or IEEE 802.11 wireless fidelity "Wi-Fi" interfacing standards. Other configurations and combinations of patient data source interfacing are possible.

The external system 105 may include an external device 106 in proximity of the one or more ambulatory medical devices, and a remote device 108 in a location relatively distant from the one or more ambulatory medical devices, in communication with the external device 106 via a communication network 107. Examples of the external device 106 may include a medical device programmer. The remote device 108 can be configured to evaluate collected patient or patient information and provide alert notifications, among other possible functions. In an example, the remote device 108 may include a centralized server acting as a central hub for collected data storage and analysis. The server can be configured as a uni-, multi-, or distributed computing and processing system. The remote device 108 can receive data from multiple patients. The data can be collected by the one or more ambulatory medical devices, among other data acquisition sensors or devices associated with the patient 101. The server may include a memory device to store the data in a patient database. The server may include an alert analyzer circuit to evaluate the collected data to determine if specific alert condition is satisfied. Satisfaction of the alert condition may trigger a generation of alert notifications, such to be provided by one or more human-perceptible user interfaces. In some examples, the alert conditions may alternatively or additionally be evaluated by the one or more ambulatory medical devices, such as the implantable medical device. By way of example, alert notifications may include a Web page update, phone or pager call, E-mail, SMS, text or "Instant" message, as well as a message to the patient and a simultaneous direct notification to emergency services and to the clinician. Other alert notifications are possible. The server may include an alert prioritizer circuit configured to prioritize the alert notifications. For example, an alert of a detected physiological event can be prioritized using a similarity metric between the physiological data associated with the detected physiological event to physiological data associated with the historical alerts.

The remote device 108 may additionally include one or more locally configured clients or remote clients securely connected over the communication network 107 to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 108, including the server and the interconnected clients, may also execute a follow-up scheme by sending follow-up requests to the one or more ambulatory medical devices, or by sending a message or other communication to the patient 101 (e.g., the patient), clinician or authorized third party as a compliance notification.

The communication network 107 can provide wired or wireless interconnectivity. In an example, the communication network 107 can be based on the Transmission Control Protocol/Internet Protocol (TCP/IP) network communication specification, although other types or combinations of networking implementations are possible. Similarly, other network topologies and arrangements are possible.

One or more of the external device 106 or the remote device 108 can output the detected physiological events to a system user, such as the patient or a clinician, or to a process including, for example, an instance of a computer program executable in a microprocessor. In an example, the process may include an automated generation of recommendations for anti-arrhythmic therapy, or a recommendation for further diagnostic test or treatment. In an example, the external device 106 or the remote device 108 may include a respective display unit for displaying the physiological or functional signals, or alerts, alarms, emergency calls, or other forms of warnings to signal the detection of arrhythmias. In some examples, the external system 105 may include an external data processor configured to analyze the physiological or functional signals received by the one or more ambulatory medical devices, and to confirm or reject the detection of arrhythmias. Computationally intensive algorithms, such as machine-learning algorithms, can be implemented in the external data processor to process the data retrospectively to detect cardia arrhythmias.

Portions of the one or more ambulatory medical devices or the external system 105 can be implemented using hardware, software, firmware, or combinations thereof. Portions of the one or more ambulatory medical devices or the external system 105 can be implemented using an application-specific circuit that can be constructed or configured to perform one or more functions or can be implemented using a general-purpose circuit that can be programmed or otherwise configured to perform one or more functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. "Sensors" may include electronic circuits configured to receive information and provide an electronic output representative of such received information.

The therapy device 110 can be configured to send information to or receive information from one or more of the ambulatory medical devices or the external system 105 using the communication link 111. In an example, the one or more ambulatory medical devices, the external device 106, or the remote device 108 can be configured to control one or more parameters of the therapy device 110. The external system 105 can allow for programming the one or more ambulatory medical devices and can receives information about one or more signals acquired by the one or more ambulatory medical devices, such as can be received via a communication link 111. The external system 105 may include a local external implantable medical device programmer. The external system 105 may include a remote patient management system that can monitor patient status or adjust one or more therapies such as from a remote location.

Figure 2:
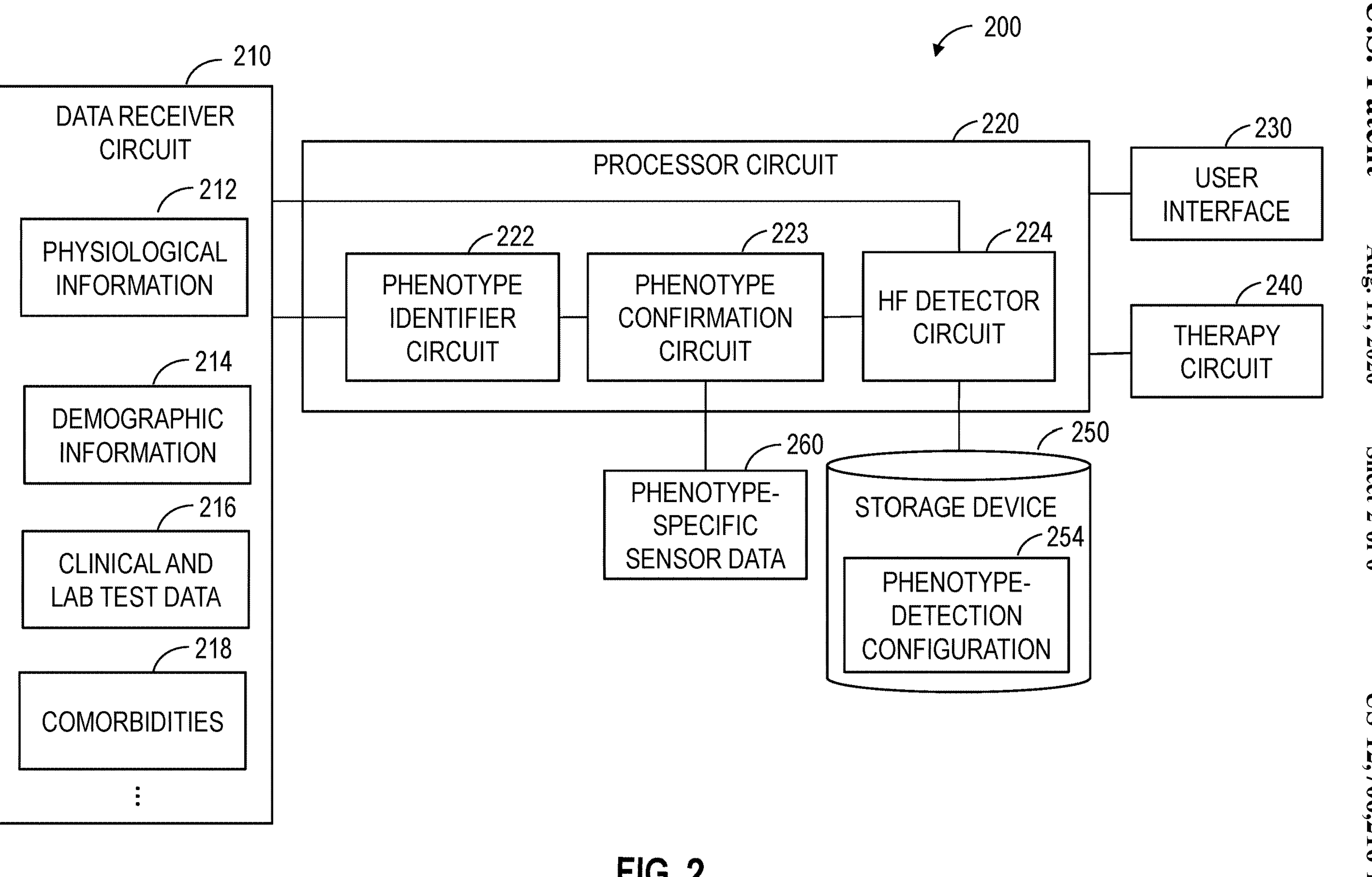
FIG. 2 illustrates generally an example of a heart failure monitor system configured to detect a heart failure status based on phenotype classification in a patient.

FIG. 2 illustrates generally an example of a heart failure monitor system 200 configured to detect a heart failure status based on phenotype classification in a patient. The heart failure monitor system 200 may include one or more of a data receiver circuit 210, a processor circuit 220, a user interface 230, a therapy circuit 240, and a storage device 250. At least a portion of the system 200 may be implemented in the IMD 102, the WMD 103, or the external system 105 such as one or more of the external device 106 or the remote device 108.

The data receiver circuit 210 may receive physiological information 212 from a patient. In an example, the data receiver circuit 210 may be coupled to a sensor or electrode (s) to sense the physiological information 212, such as an implantable, wearable, or otherwise ambulatory sensor or electrodes associated with the patient. The sensor may be incorporated into or associated with an ambulatory device such as the IMD 102 or the WMD 103. Examples of the physiological information 212 may include surface electrocardiography from electrodes placed on the body surface, subcutaneous ECG sensed from electrodes placed under the skin, intracardiac electrogram (EGM), heart rate signal, physical activity signal, or posture signal, a thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal, physiological response to activity, apnea hypopnea index, one or more respiration signals such as a respiratory rate signal or a tidal volume signal, brain natriuretic peptide, blood panel, sodium and potassium levels, glucose level and other biomarkers and bio-chemical markers, among others. In some examples, the physiological information 212 sensed from a patient may be stored in a storage device, such as an electronic medical record (EMR) system. The data receiver circuit 210 may receive the physiological information 212 from the storage device, such as in response to a user command or a triggering event.

In an example, the physiological information 212 may include heart sound information sensed by a heart sound sensor from the patient. The heart sound information may include one or more of S1, S2, S3, or S4 heart sound components. In an example, the heart sound information may include a body motion/vibration signal indicative of cardiac vibration, which is correlated to or indicative of heart sounds. Examples of the heart sound sensor may include an accelerometer, an acoustic sensor, a microphone, a piezo-based sensor, or other vibrational or acoustic sensors. The accelerometer can be a one-axis, a two-axis, or a three-axis accelerometer. Examples of the accelerometer may include flexible piezoelectric crystal (e.g., quartz) accelerometer or capacitive accelerometer, fabricated using micro electro-mechanical systems (MEMS) technology. The heart sound sensor may be included in the IMD 102 or the WMD 103, or disposed on a lead such as a part of the lead system associated with the IMD 102 or the WMD 103. In an example, an accelerometer (or other sensors) may sense an epicardial or endocardial acceleration (EA) signal from a portion of a heart, such as on an endocardial or epicardial surface of one of a left ventricle, a right ventricle, a left atrium, or a right atrium. The EA signal may contain components corresponding to various heart sound components such as one or more of S1, S2, S3, or S4 components.

The data receiver circuit 210 may additionally receive patient clinical information including, for example, one or more of a patient demographic information 214, heart failure comorbid conditions 216, or clinical and lab tests data 218. Examples of the patient demographic information 214 may include age, gender, race, among other socioeconomic information. Examples of the heart failure comorbid conditions 216 may include diabetes, kidney dysfunction (e.g., chronic kidney disease, or CKD), pulmonary disease (e.g., chronic obstructive pulmonary disease, or COPD), cardiac arrhythmia (e.g., atrial fibrillation), cardiac diastolic dysfunctions, hypertension, autonomic dysfunctions, obesity, metabolic disorders, skeletal muscle weakness, among others. The clinical and lab tests data 218 in relation to heart failure may include, for example, blood urea nitrogen (BUN) level, thiamine pyrophosphate (TPP) level, or other blood chemistry. Other patient information received by the data receiver circuit 210 may include patient vital signs, medical history including prior medical or surgical treatment, dietary and physical activity patterns, weight, etc. Such patient information, collectively referred to as clinical information in this document, may be provided by the user (e.g., the patient or a clinician) via the user interface 230, or received automatically in response to a triggering event, such as a change in the medical history or medication of the patient.

The processor circuit 220 may detect a heart failure status in a patient using physiological information 212 and optionally other clinical information such as one or more of the patient demographic information 214, the heart failure comorbid conditions 216, or the clinical and lab tests data 218. In an example, the processor circuit 220 can detect a HFpEF status. The processor circuit 220 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The processor circuit 220 may include circuit sets comprising one or more other circuits or sub-circuits including a phenotype identifier circuit 222, a phenotype confirmation circuit 223, and a heart failure detector circuit 224, These circuits or sub-circuits may, either individually or in combination, perform the functions, methods or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The phenotype identifier circuit 222 may classify the patient into one of a plurality of heart failure phenotypes using the received physiological information 212 and patient clinical information such as one or more of the patient demographic information 214, the heart failure comorbid conditions 216, or the clinical and lab tests data 218. A heart failure phenotype can be characterized by a group of features related to heart failure, which may include patient vital signs, multi-dimensional patient demographic information, medical history, dietary and physical activity patterns, weight, heart failure comorbid conditions, clinical and lab test data, patient medication information, sensor signals recorded by implantable or wearable sensors or signal metrics derived from the sensor signals, among others.

Patients classified into different phenotypes may have different heart failure event rate, represented by the amount of heart failure events within a specified time period (e.g., a month, or several months). For example, patients in phenotype $P_1$ may experience more frequent heart failure events than patients in phenotype $P_2$. A heart failure detector, when applied to patients with different phenotypes, may result in different detection performance (e.g., different sensitivity, specificity, positive predictive value, or negative predicative value). For example, while patients in phenotype $P_2$ may experience a lower heart failure event rate than patients in phenotype $P_1$, a heart failure detector, when applied to patients in $P_2$ and $P_1$, may produce significantly more alerts of heart failure detections in the patients of phenotype $P_2$ than patients in phenotype $P_1$. That is, more false positive detections (thus a lower specificity) may have occurred to patients of phenotype $P_2$ than patients in phenotype $P_1$. Adjusting a heart failure detector based on patient phenotype, or choose different heart failure detectors indicated by patient phenotype, may reduce false positive detections or false alerts while maintaining or improving detection sensitivity, thereby improving overall performance of heart event detections in a wide range of patients.

Figures 3A, 3B:
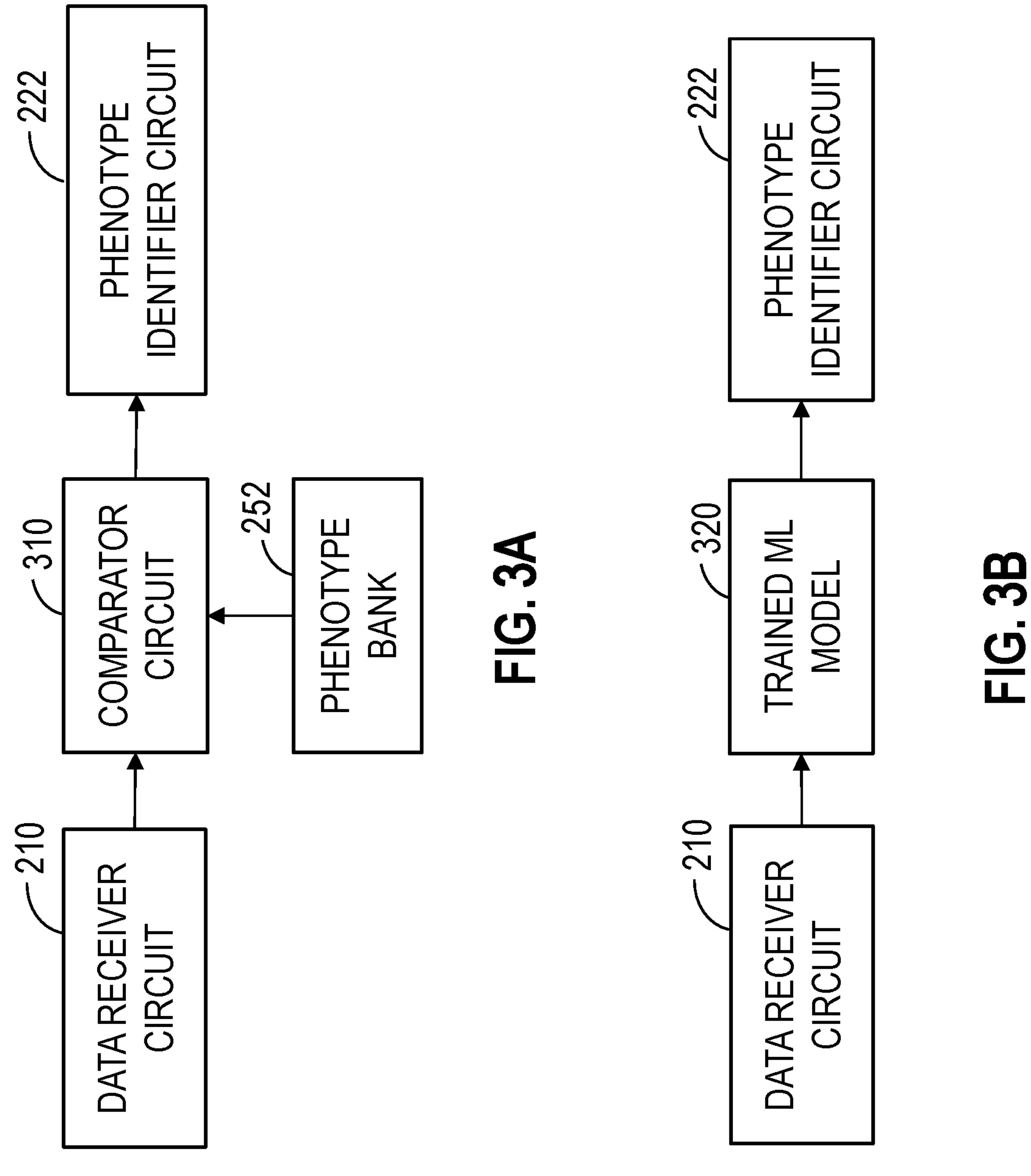
FIGS. 3A-3B illustrate generally example approaches for recognizing a target heart failure phenotype for a patient.

The phenotype identifier circuit 222 may recognize a target heart failure phenotype (P*) for the patient using the physiological information 212 and optionally one or more types of clinical information such as the patient demographic information 214, the heart failure comorbid conditions 216, or the clinical and lab tests data 218. FIGS. 3A-3B illustrate, by way of example and not limitation, approaches for recognizing the target heart failure phenotype P* for the patient. In the example as shown in FIG. 3A, the phenotype identifier circuit 222 can access a phenotype bank 252 established and maintained in the storage device 250. The phenotype bank 252 stores a plurality of predetermined heart failure phenotypes $\{P_1, P_2, \ldots, P_N\}$. Each predetermined phenotype can be characterized by one or more patient attributes or features including, for example, patient demographics, medical history, medication intake and dosage, clinical and laboratory test results, heart failure comorbidities, physiological sensor data, among others. The number and/or types of the patient attributes or features may differ from one phenotype to another. The patient attributes or features in a phenotype may have a numerical value or a range of numerical values (e.g., age=45-55 years old), or a categorical value (e.g., race=Caucasian).

The phenotype identifier circuit 222 may be electrically coupled to a comparator circuit 310 that can determine a similarity metric between the received patient physiological and clinical information (received by the data receiver circuit 210) and one or more of the predetermined heart failure phenotypes in the phenotype bank 252. Each phenotype may have a cluster center characterized by representative feature values of physiological sensor output, demographic information, comorbid conditions, clinical and lab tests results, etc. The similarity metric can include, for example, a distance between the patient physiological and clinical information and each cluster center in the multi-dimensional feature space. The phenotype identifier circuit 222 may identify a target phenotype as one with a shortest distance (thus the highest level of similarity). Examples of the distance metric may include Euclidean distance, Mahalanobis distance, correlation coefficient, or a L1, L2, or infinite norm, among others.

FIG. 3B shows a portion of a system for recognizing the target phenotype P* using machine learning (ML) or artificial intelligence (AI). To recognize the target phenotype P*, the phenotype identifier circuit 222 may apply the received patient physiological and clinical information (as produced by the data receiver circuit 210) to at least one trained ML model 320 being trained to establish a correspondence between an input of patient physiological and clinical information and an output of a heart failure phenotype. The trained ML model 320 may be trained using supervised learning or unsupervised learning techniques. Supervised learning uses prior knowledge (e.g., examples that correlate inputs to outputs or outcomes) to learn the relationships between the inputs and the outputs. The goal of supervised learning is to learn a function that, given some training data, best approximates the relationship between the training inputs and outputs so that the ML model can implement the same relationships when given inputs to generate the corresponding outputs. Some examples of commonly used supervised-ML algorithms are Logistic Regression (LR), Naive-Bayes, Random Forest (RF), neural networks (NN), deep neural networks (DNN), matrix factorization, and Support Vector Machines (SVM). Examples of DNN include a convolutional neural network (CNN), a recurrent neural network (RNN), a deep belief network (DBN), or a hybrid neural network comprising two or more neural network models of different types or different model configurations. Unsupervised learning is the training of an ML algorithm using information that is neither classified nor labeled, and allowing the algorithm to act on that information without guidance. Unsupervised learning is useful in exploratory analysis because it can automatically identify structure in data. Some common tasks for unsupervised learning include clustering, representation learning, and density estimation. Some examples of commonly used unsupervised learning algorithms are K-means clustering, principal component analysis, and autoencoders.

Referring back to FIG. 2, the phenotype confirmation circuit 223 can confirm or modify the target heart failure phenotype P* (such as identified from the phenotype bank 252) using phenotype-specific sensor data 260. The phenotype-specific sensor can be a sensor optimized for (e.g., with a high detection sensitivity or specificity) detecting heart failure status (e.g., HFpEF) in patients of a certain phenotype, and can be determined using data from a patient population classified as having such phenotype. Table 1 below provides non-limiting examples of the phenotype-specific sensor that may be used to confirm various HFpEF phenotypes characterized by, for example, respective heart failure comorbidities.

TABLE 1

| HFpEF Phenotypes | Phenotype-Specific Sensors | Signal Metrics for Confirming Phenotypes |
|---|---|---|
| Atrial fibrillation (AF) | AF detector, HR sensor | AF burden |
| Hypertension | Pressure sensor, heart sound sensor | BP, S2 morphology |
| Diastolic Dysfunction | Heart sound sensor | S3 intensity |
| Renal Dysfunction | Blood chemical sensor | Blood sodium level, etc. |
| Skeletal Muscle Weakness | Activity sensor, respiration sensor, oximetry sensor | Respiration rate, arteriovenous oxygen level |

As shown in Table 1, the phenotype-specific sensors can include, for example, AF or heart rate sensors for an AF phenotype, a blood pressure sensor or a heart sound sensor (specifically for detecting S2 heart sound morphology which is correlated to the magnitude of central aortic reflection wave predictive of HFpEF) for a hypertension phenotype, a heart sound sensor (specifically for detecting S3 heart sound) for a diastolic dysfunction phenotype, a blood chemical sensor (specifically for detecting sodium excretion as an example) for a renal dysfunction phenotype, or one or more of activity sensor, respiration sensor, or oximetry sensor for a phenotype of skeletal muscle weakness characterized by exercise intolerance and deficiency of arteriovenous oxygen saturation level during exercise. The phenotype identifier circuit 222 may first classify the patient into a "preliminary" heart failure phenotype P*, such as the target heart failure phenotype recognized from the phenotype bank 252 as described above, using the patient's baseline physiological and clinical information, such as a 30-day moving average of physiological sensor data. The phenotype identifier circuit 222 can then confirm or modify the "preliminary" heart failure phenotype P* using sensor output from the phenotype-specific sensor specific to the "preliminary" heart failure phenotype P*. For example, AF event rate or AF burden, or heart rates may be used to confirm an AF phenotype, a pressure or S2 morphology may be used to confirm a hypertension phenotype, S3 intensity may be used to confirm a diastolic dysfunction phenotype, a blood chemistry tests may be used to confirm a renal dysfunction phenotype, or respiration rate and arteriovenous oxygen level (detected by the oximetry sensor) to confirm skeletal muscle weakness phenotype. Based on the phenotype-specific sensor data 260, a severity of a symptom or a comorbid condition associated with the classified phenotype P* can be assigned to the confirmed phenotype. The severity can be represented by a numerical score or a categorical level.

The heart failure detector circuit 224 can determine a heart failure detection setting (DX*) for the patient based on the recognized target heart failure phenotype (P*), or the phenotype confirmed by the phenotype confirmation circuit 223. A detection setting, as described in this document, may include one or more of physiological signals (e.g., sensor outputs) or signal metrics, values of one or more detection parameters, or detection architecture or algorithms. Selecting different settings may include selectively activating or deactivating a physiological sensor for sensing and acquiring respective physiological signal, selecting certain portions of a physiological signal (such as when the patient undergoes a particular physical activity level or during a particular time of day, or under other specified conditions), selecting different signal metrics. Different detection settings may differ in a detection threshold value to which a signal index or a composite index is compared to determine the heart failure status. Different detection settings may additionally or alternatively differ in detection architectures (e.g., decision trees, neural networks, support vector machines, logistic regression, naive-Bayes, random forests, deep neural networks, among others), or parameter values in such detection architectures such as weights assigned to respective signal metrics to compute a composite index. When the heart failure phenotype P* has changed from one phenotype to another, the heart failure detector circuit 224 can automatically adjust the heart failure detection setting accordingly. This advantageously ensures that the heart failure detection is phenotype-specific and tailored to meet an individual patient's changing condition.

Figure 4:
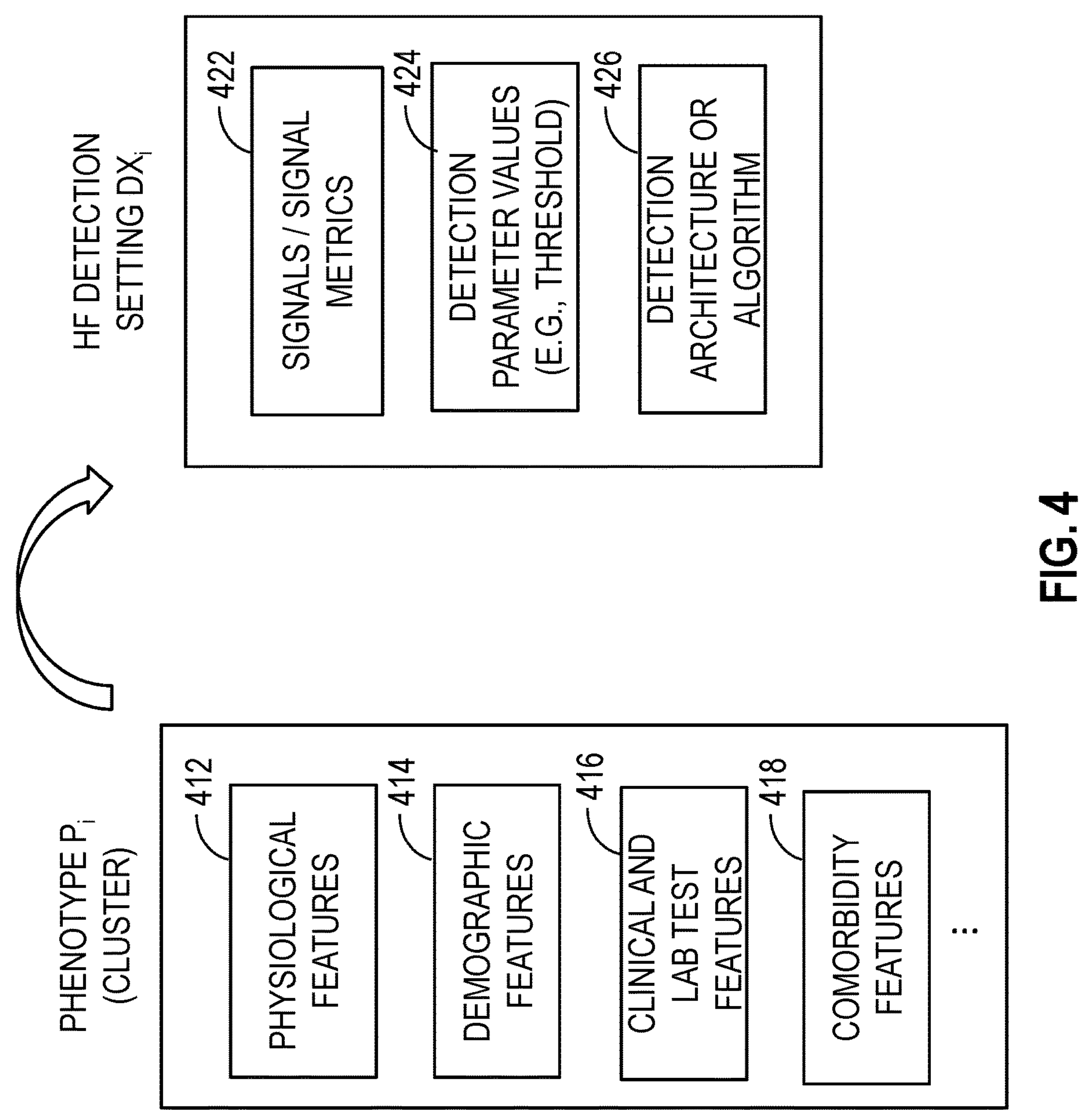
FIG. 4 illustrates generally an example of a phenotype-detection setting map.

The determination or adjustment of the heart failure detection setting can be carried out using a phenotype-detection setting map 254 stored in the storage device 250. The phenotype-detection setting map 254 represents a correspondence between a plurality of heart failure phenotypes $\{P_1, P_2, \ldots, P_N\}$ and respective predetermined detection settings $\{DX_1, DX_2, \ldots, DX_N\}$. Each detection setting $DX_i$ may include a detection setting optimized for detecting a heart failure status (e.g., HFpEF) in patients classified into heart failure phenotype $P_i$. Referring to FIG. 4, the diagram 400 shows an example of the phenotype-detection setting map 254, where each phenotype $P_i$ is mapped to the corresponding detection setting $DX_i$. Each phenotype $P_i$ may be characterized by a cluster of physiological and clinical features in a multi-dimensional feature space, including one or more of physiological features 412, demographic features 414, clinical and lab test features 416, or comorbidity features 418, among others. Such physiological and clinical features characterizing the phenotype $P_i$ can be similar to the physiological and clinical information received from the patient by the data receiver circuit 210, as described above with respect to FIG. 1. The corresponding detection setting $DX_i$, as described above, may include one or more of physiological signals (e.g., sensor outputs) or signal metrics 422, values of one or more detection parameters (such as threshold values for a signal index or a composite signal index) 424, or a detection architecture or algorithm 426. The phenotype-detection setting map 254 may be constructed using information about heart failure phenotypes and heart failure detection performances (e.g., sensitivity, specificity, or positive predictive values) collected from a patient population being classified into the same phenotype. The optimal parameter setting for a particular phenotype may be determined as one that leads to a heart failure detection performance satisfying a specific condition using data collected from the patient population having that same phenotype.

In some examples, the phenotype identifier circuit 222 may compute a patient phenotype score ($S_X$) using attributes of the received patient information (e.g., the physiological information 212, the patient demographic information 214, the heart failure comorbid conditions 216, or the clinical and lab tests data 218). Each attribute that satisfies a specific condition (e.g., exceeding a threshold, falling within a value range, or being categorized into a specific category) may be assigned an attribute score (i.e., a numerical value). The phenotype-detection setting map 254 may map a phenotype score or a score range ($S_i$) to a detection setting ($DX_i$). In an example, a larger phenotype score $S_i$ may be mapped to a detection setting $DX_i$ that corresponds to a detection algorithm having a higher sensitivity, such that false negatives or miss of heart failure detection may be reduced. A smaller phenotype score $S_j$ may be mapped to a detection setting $DX_j$ that corresponds to a detection algorithm having a higher specificity, such that false positive heart failure detection may be reduced. The phenotype identifier circuit 222 can use the phenotype-detection setting map 254 to determine the target detection setting (DX*) that corresponds to the phenotype score ($S_X$) computed for the patient using the attributes of the received patient information.

The heart failure detector circuit 224 can detect a heart failure status in the patient by applying patient information, such as the physiological information 212, to the phenotype-specific detection setting DX*. In an example, the physiological information 212 include one or more physiological signals sensed using respective sensors, and the heart failure detector circuit 224 may generate one or more signal metrics from the sensed physiological signal. The signal metrics may include statistical or morphological features. By way of example and not limitation, the signal metrics may include heart rate, heart rate variability, cardiac activation timings, morphological features from the ECG or EGM, thoracic or cardiac impedance magnitude within a specified frequency range, intensities or timings of S1, S2, S3, or S4 heart sounds, systolic blood pressure, diastolic blood pressure, mean arterial pressure, or timing of a pressure metric with respect to a fiducial point, among others. In various examples, the signal metrics may be trended over time.

In an example, the heart failure detector circuit 224 may detect a heart failure status by comparing a signal metric to a detection threshold as specified in the detection setting DX*. In some examples, the detection setting DX* represents a personalized, phenotype-specific detection algorithm that computes composite signal index (also referred to as a heart failure index) using a combination, such as a linear weighted combination, of two or more signal metrics derived from the one or more physiological signals, and determining whether the composite signal index satisfies a predetermined condition. Examples of such signal metrics may include heart sound metrics, thoracic impedance metrics, respiration metrics such as respiration rate or volume, physical activity metrics such as activity intensity or activity duration, heart rates at certain time of the day such as nocturnal heart rates, blood pressure metrics, oxygen saturation levels, cardiac arrhythmia (e.g., AF) burden, chemical or biomarker metrics, among others. A heart failure diagnosis is generated in response to the composite signal index satisfying the predetermined condition, such as exceeding a threshold. The predetermined condition, the detection threshold, and the two or more signal metrics selected for computing the composite signal index may be specified to detection setting DX*.

In the case that the detection setting includes a composite signal index computed using a weighted combination of selected signal metrics each scaled by respective weights, the heart failure detector circuit 224 can adjust the weights for one or more signal metrics. Generally, signal metrics derived from sensor output that is highly correlated to a specific symptom or comorbid condition can be assigned with a higher weight. For example, if the patient phenotype includes an attribute of significant shortness of breath, the corresponding detection setting DX may include a larger weight assigned to respiration rate (RR) trend for constructing a composite index for heart failure detection. In another example, if the patient phenotype includes an attribute of significant palpitation, the corresponding detection setting DX may include a larger weight assigned to heart rate trend for constructing a composite index for heart failure detection. If the patient phenotype include an attribute of arrhythmia event rate (e.g., AF), the corresponding detection setting DX may include a larger weight assigned to AF event rate or AF burden. Yet in another example, if the patient phenotype includes an attribute of edema (such as due to long-term standing), the corresponding detection setting DX may include a larger weight assigned to total thoracic impedance for constructing a composite index for heart failure detection.

In some examples, signal metrics derived from the phenotype-specific sensors can be included in the signal metrics used for computing the composite signal index, and be assigned with higher weights than signal metrics derived from other sensors. In some examples, the heart failure detector circuit 224 can adjust the weights for respective signal metrics based on the severity of symptom or comorbid condition associated with the phenotype determined during the phenotype confirmation by the phenotype confirmation circuit 223. For example, when S3 heart sound intensity is used to confirm the diastolic dysfunction phenotype, the heart failure detector circuit 224 can reduce the weight for S3 intensity if the patient has normal or mild diastolic dysfunction, and increase the weight for S3 intensity if the patient has moderate or severe diastolic function.

In some examples, the heart failure detector circuit 224 may process the signal metric trend and generate a predictor trend indicating temporal changes of the signal metric trend. The temporal change may be calculated using a difference between short-term values and baseline values. In an example, the short-term values may include statistical values such as a central tendency of the measurements of the signal metric within a short-term window of a first plurality of days. The baseline values may include statistical values such as a central tendency of the measurements of the signal metric within a long-term window of a second plurality of days preceding the short-term window in time. The parameters used for computing the short-term and long-term value may be specified in the phenotype-specific detection setting DX*. In some examples, the predictor trend may be determined using a linear or nonlinear combination of the relative differences between multiple short-term values corresponding to multiple first time windows and multiple baseline values corresponding to multiple second time windows. The differences may be scaled by respective weight factors which may be based on timing information associated with corresponding multiple short-term window, such as described by Thakur et al., in U.S. Patent Publication 2017/0095160, entitled "PREDICTIONS OF WORSENING HEART FAILURE", which is herein incorporated by reference in its entirety. In some examples, the heart failure detector circuit 224 may predict a time to heart failure event using the predictor trend. The predicted time to heart failure event may be provided to a user (e.g., a clinician) or an automated patient management system to generate a personalized, chronic patient management plan. In some examples, the heart failure detector circuit 224 may monitor patient acute responses to treatment (e.g., drug therapy or electrostimulation therapy), titrate therapy dosage, or determine patient readiness to discharge or readmission in accordance with the predictor trend.

In some examples, the system 200 can be configured to detect a particular type of heart failure, such as heart failure with preserved ejection fraction (HFpEF). The phenotype identifier circuit 222 can classify the patient into one of a plurality of predetermined HFpEF phenotypes using the received physiological and clinical information. In an example, the phenotype-detection setting map 254 includes a correspondence between the plurality of predetermined HFpEF phenotypes and the detection parameter values, such as weights for signal metrics used for computing the composite signal index, or an S3 intensity threshold values. Examples of the predetermined HFpEF phenotypes may include phenotypes with predominant heart failure comorbid conditions, such as an arrhythmia (e.g., atrial fibrillation, or AF), hypertension, cardiac diastolic dysfunction, renal dysfunction, among others. As described above, the phenotype P* recognized for the patient may be confirmed using phenotype-specific sensor data 260, such as those shown in Table 1.

The heart failure detector circuit 224 can determine or adjust a detection setting for detecting HFpEF based on the classified phenotype ($P_X$) or the confirmed phenotype. The heart failure detector circuit 224 can use the phenotype-detection setting map 254 to determine a target detection setting corresponding to the phenotype ($P_X$), such as a composite signal index computed using a weighted combination of selected signal metrics each scaled by respective weights or weight ranges, and/or a target S3 intensity threshold value. The heart failure detector circuit 224 can detect whether the patient has developed HFpEF using heart sound information sensed from the patient, such as S3 sound intensity, optionally among other physiological information. For example, heart failure detector circuit 224 can generate a diagnostic of HFpEF for the patient if the S3 sound intensity exceeds the phenotype-specific S3 intensity threshold.

The detected heart failure status, or a human-perceptible notification of the detection of the heart failure status, may be presented to a user via the user interface 230, such as being displayed on a display screen. Also displayed or otherwise presented to the user via the user interface 230 may include one or more of the sensed physiological signal, signal metrics, patient heart failure phenotype $P_X$, target phenotype P* recognized from the phenotype bank, and the detection settings DX*, among other intermediate measurements or computations. The information may be presented in a table, a chart, a diagram, or any other types of textual, tabular, or graphical presentation formats. The presentation of the output information may include audio or other media format. In an example, alerts, alarms, emergency calls, or other forms of warnings may be generated to signal the system user about the detected heart failure status.

The optional therapy circuit 240 may be configured to deliver a therapy to the patient in response to the detected heart failure status. Examples of the therapy may include electrostimulation therapy delivered to the heart, a nerve tissue, other target tissues, a cardioversion therapy, a defibrillation therapy, or drug therapy including delivering drug to a tissue or organ. In some examples, the therapy circuit 240 may modify an existing therapy, such as adjust a stimulation parameter or drug dosage.

Although the discussion herein focuses on heart failure detection, this is meant only by way of example but not limitation. Systems, devices, and methods discussed in this document may also be suitable for detecting various sorts of diseases or for assessing risk of developing other worsened conditions, such as cardiac arrhythmias, heart failure decompensation, pulmonary edema, pulmonary condition exacerbation, asthma and pneumonia, myocardial infarction, dilated cardiomyopathy, ischemic cardiomyopathy, valvular disease, renal disease, chronic obstructive pulmonary disease, peripheral vascular disease, cerebrovascular disease, hepatic disease, diabetes, anemia, or depression, among others.

Figure 5:
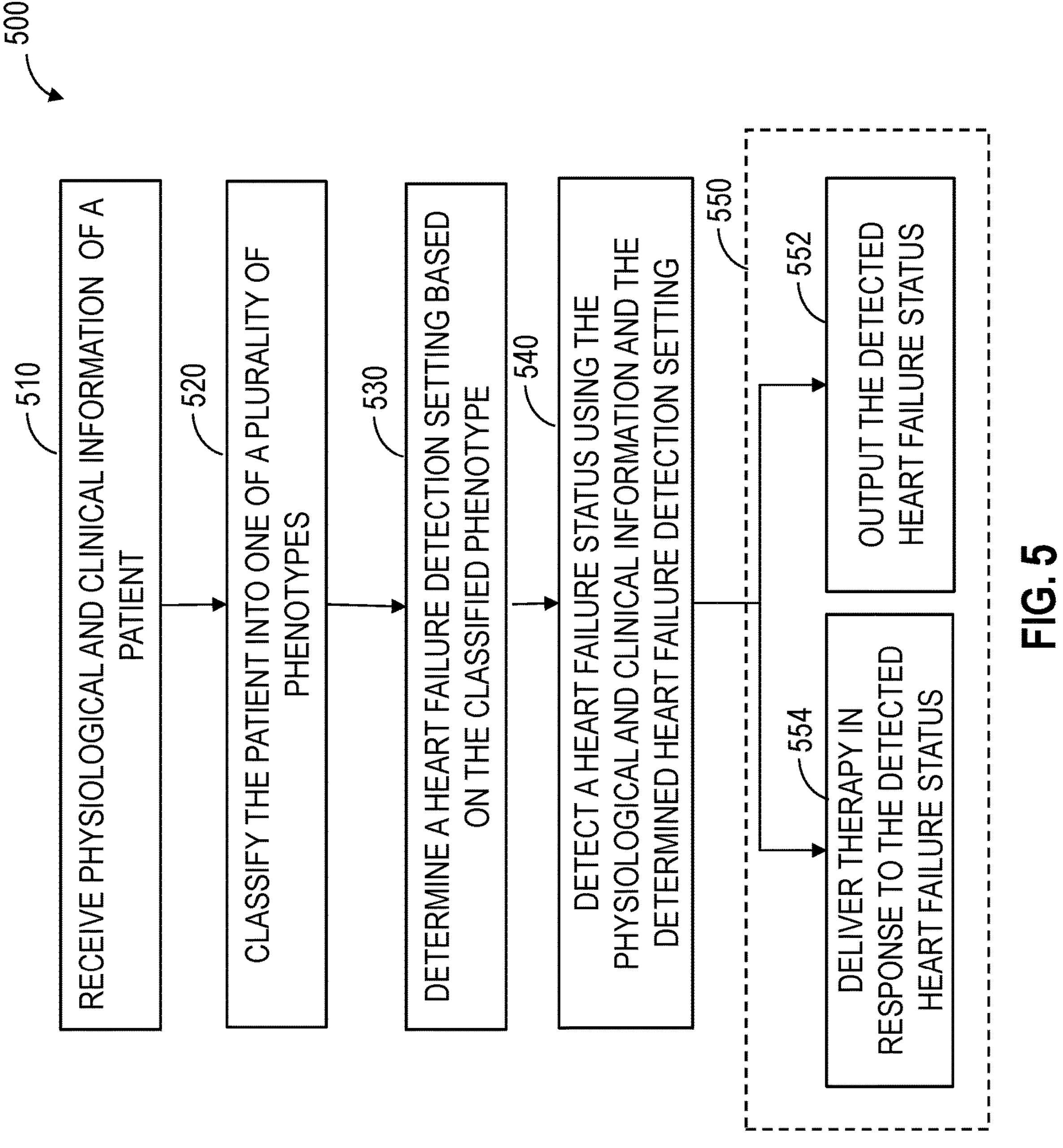
FIG. 5 illustrates generally an example of a method for detecting a heart failure status based on phenotype classification in a patient.

FIG. 5 illustrates generally an example of a method 500 for detecting a heart failure status in a patient based on phenotype classification. The method 500 may be implemented and executed in an ambulatory medical device, such as an implantable or wearable medical device, or in a remote patient management system. In various examples, the method 500 may be implemented in and executed by the IMD 102 or the WMD 103, one or more devices in the external system 105, or the heart failure monitor system 200 or a modification thereof.

The method 500 commences at step 510, where physiological and clinical information from a patient may be received. Examples of the physiological information may include ECG, EGM, heart rate signal, physical activity signal, or posture signal, a thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal, physiological response to activity, apnea hypopnea index, one or more respiration signals such as a respiratory rate signal or a tidal volume signal, brain natriuretic peptide, blood panel, sodium and potassium levels, glucose level and other biomarkers and bio-chemical markers, among others. In an example, the physiological signal may be sensed and acquired using a sensor circuit coupled to one or more implantable, wearable, or otherwise ambulatory sensors or electrodes associated with the patient. Alternatively, the physiological information may be acquired and stored in a storage device, such as an electronic medical record system, and may be retrieved in response to a user input or triggered by a specific event. The received clinical information may include, for example, patient demographic information (e.g., age, gender, race, or socioeconomic information), or heart failure comorbid conditions (e.g., diabetes, kidney dysfunction, pulmonary disease, cardiac arrhythmia, cardiac diastolic dysfunctions, hypertension, autonomic dysfunctions, obesity, metabolic disorders, skeletal muscle weakness, blood chemistry test results, patient vital signs, medical history, dietary and physical activity patterns, weight, or may also be received. Such clinical information may be provided by the user (e.g., the patient or a clinician) or received automatically in response to a triggering event, such as a change in the medical history or medication of the patient.

At 520, the patient may be classified into one of a plurality of heart failure phenotypes based on the received physiological and clinical information, such as using the phenotype identifier circuit 222. Such patient classification process is also referred to as identifying a target heart failure phenotype (P*) for the patient. A heart failure phenotype can be characterized by a group of features related to heart failure, which may include patient vital signs, multi-dimensional patient demographic information, medical history, dietary and physical activity patterns, weight, heart failure comorbid conditions, clinical and lab test data, patient medication information, sensor signals recorded by implantable or wearable sensors or signal metrics derived from the sensor signals, among others.

The target heart failure phenotype (P*) may be identified for the patient using approaches such as those described above with reference to FIGS. 3A-3B. In an example, the target phenotype P* may be identified by searching a phenotype bank for a predetermined phenotype that matches the received patient heart failure phenotype ($P_X$) using a pattern recognition method. In an example, a similarity metric between the received patient physiological and clinical information and one or more of the predetermined heart failure phenotypes in the phenotype bank can be computed. Each phenotype may have a cluster center characterized by representative feature values of physiological sensor output, demographic information, comorbid conditions, clinical and lab tests results, etc. The similarity metric can include, for example, a distance between the patient physiological and clinical information and each cluster center in the multi-dimensional feature space. The phenotype identifier circuit 222 may identify a target phenotype as one with a shortest distance (thus the highest level of similarity). In another example, the target phenotype P* may be recognized using a machine learning (ML) or artificial intelligence (AI) based method. In an example, the received patient physiological and clinical information may be applied to at least one trained ML model. Such ML model may be trained using supervised learning or unsupervised learning techniques to establish a correspondence between an input of patient physiological and clinical information and an output of a heart failure phenotype.

In some examples, the target heart failure phenotype P* may be confirmed or modified using information from at least one phenotype-specific sensor, such as one of those as shown in Table 1. As described above, for example, AF event rate or AF burden or heart rates may be used to confirm an AF phenotype, a pressure or S2 morphology may be used to confirm a hypertension phenotype, S3 intensity may be used to confirm a diastolic dysfunction phenotype, a blood chemistry tests may be used to confirm a renal dysfunction phenotype, or respiration rate and arteriovenous oxygen level (detected by the oximetry sensor) to confirm skeletal muscle weakness phenotype. Based on the phenotype-specific sensor output, a severity of a symptom or a comorbid condition associated with the classified phenotype P* can be assigned to the confirmed phenotype.

At 530, a heart failure detection setting (DX*) can be determined for the patient based on the recognized target heart failure phenotype (P*), or the phenotype confirmed by the phenotype-specific sensor, such as using the heart failure detector circuit 224. The detection setting may include one or more of physiological signals (e.g., sensor outputs) or signal metrics, values of one or more detection parameters, or detection architecture or algorithms. Different detection settings may differ in detection architectures, or parameter values in such detection architectures such as weights assigned to respective signal metrics to compute a composite index. When the heart failure phenotype P* has changed from one phenotype to another, the heart failure detection setting may be adjusted accordingly. This advantageously ensures that the heart failure detection is phenotype-specific and tailored to meet an individual patient's changing condition. In an example, the determination or adjustment of the heart failure detection setting can be carried out using a phenotype-detection setting map representing a correspondence between a plurality of heart failure phenotypes and respective predetermined detection settings, such as that shown in FIG. 4. Each detection setting $DX_i$ may include a detection setting optimized for detecting a heart failure status (e.g., HFpEF) in patients classified into heart failure phenotype $P_i$. In some examples, a patient phenotype score ($S_X$) may be computed using attributes of the received patient physiological and clinical information, and the phenotype score can be mapped to a detection setting $DX_i$.

At 540, a heart failure status of the patient may be detected by applying patient physiological information to the phenotype-specific detection setting DX*. In an example, a heart failure status may be detected by comparing a signal metric to a detection threshold as specified in the detection setting DX*. In some examples, the detection setting DX* includes computing a composite signal index (also referred to as a heart failure index) using a combination, such as a linear weighted combination, of two or more signal metrics derived from the one or more physiological signals, and determining whether the composite signal index satisfies a predetermined condition, such as exceeding a detection threshold. In some examples, detection of the heart failure status may include generating a predictor trend using a difference between short-term values and baseline values. The parameters used for computing the short-term and baseline value may be specified in the detection setting DX*. The predictor trend indicates temporal changes of the signal metric trend. Alternatively, the predictor trend may be determined using a linear or nonlinear combination of the relative differences between multiple short-term values corresponding to multiple first time windows and multiple baseline values corresponding to multiple second time windows, such as described by Thakur et al., in U.S. Patent Publication 2017/0095160, entitled "PREDICTIONS OF WORSENING HEART FAILURE", which is herein incorporated by reference in its entirety. In an example, the heart failure status being detected may represent a particular type of heart failure, such as heart failure with preserved ejection fraction (HFpEF). HFpEF status may be detected using heart sound information sensed from the patient, such as S3 sound intensity, optionally among other physiological information. In an example, a diagnostic of HFpEF may be generated if the S3 sound intensity exceeds the phenotype-specific S3 intensity threshold.

At 550, the detected heart failure status, or a human-perceptible notification of the detection of the heart failure status, may be presented to a user or a process. At 552, a human-perceptible presentation of the detected heart failure status may be generated and displayed to the user. Other information such as the physiological and clinical information of the patient and signal metrics derived therefrom, the target phenotype P* determined for the patient, may also be displayed. The information may be presented in a table, a chart, a diagram, or any other types of textual, tabular, or graphical presentation formats. Hard copies of signals and information related to the heart failure detection may be generated. In an example, alerts, alarms, emergency calls, or other forms of warnings to signal the system user about the heart failure detection may be generated.

Additionally or alternatively, at 554, the detected heart failure status may trigger a therapy delivered to the patient, such as using the therapy circuit 240. Examples of the therapy may include electrostimulation therapy delivered to the heart, a nerve tissue, other target tissues, a cardioversion therapy, a defibrillation therapy, or drug therapy. In some examples, an existing therapy may be modified, such as by adjusting a stimulation parameter or drug dosage.

Figure 6:
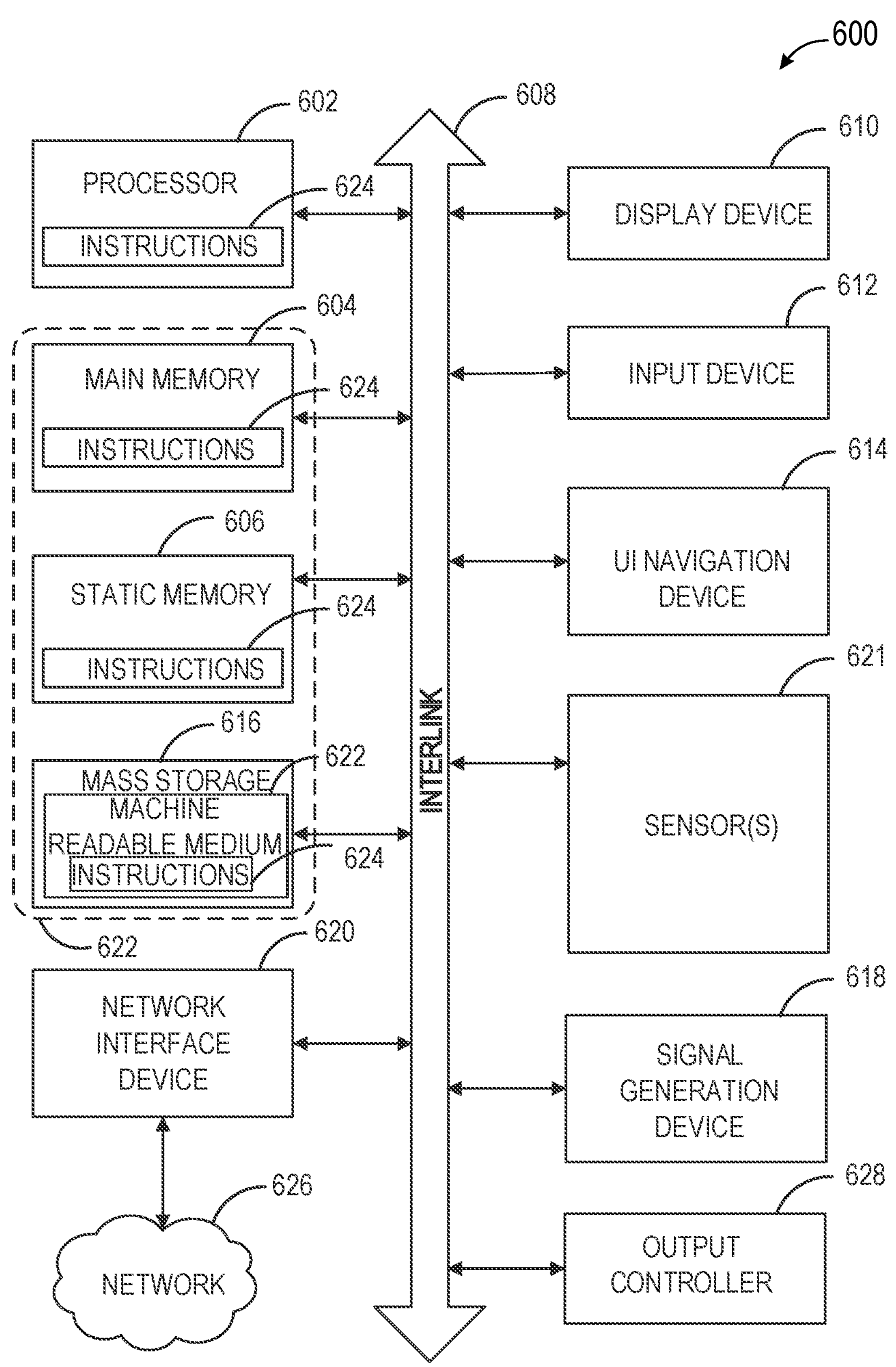
FIG. 6 illustrates generally a block diagram of an example machine upon which any one or more of the techniques discussed herein may perform.

FIG. 6 illustrates generally a block diagram of an example machine 600 upon which any one or more of the techniques (e.g., methodologies) discussed herein may perform. Portions of this description may apply to the computing framework of various portions of the IMD 102, the WMD 103, the external system 105, or the heart failure monitor system 200.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specific operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine-readable media.

While the machine-readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A medical-device system for detecting and managing heart failure in a patient, the medical-device system comprising:

a receiver circuit configured to receive physiological and clinical information of the patient; and a heart failure detector circuit configured to:

classify the patient into one of a plurality of phenotypes using the received physiological and clinical information, wherein each phenotype of the plurality of phenotypes is associated with a distinct false positive detection rate for heart failure detection;

modify one or more heart failure detection settings based on the false positive detection rate of the classified phenotype, the one or more heart failure detection settings including one or more of a detection parameter value or a detection algorithm, wherein the one or more heart failure detection settings are distinct from treatment parameters; and detect a heart failure status in the patient using the received physiological and clinical information and the modified one or more heart failure detection settings.

2. The medical-device system of claim 1, wherein the received physiological and clinical information includes heart sound information, wherein the heart failure detector circuit is configured to detect the heart failure status including a presence or absence of a heart failure with preserved ejection fraction (HFpEF) using the heart sound information and the modified one or more heart failure detection settings.

3. The medical-device system of claim 1, wherein the plurality of phenotypes are each characterized by a cluster of physiological and clinical features in a multi-dimensional feature space including at least one of:

demographic feature;

clinical or laboratory test data feature;

medical history data;

medication information;

heart failure comorbidity information; or sensor signal features produced by one or more ambulatory physiological sensors.

4. The medical-device system of claim 1, wherein the heart failure detector is configured to classify the patient into one of the plurality of phenotypes using a trained machine learning (ML) or artificial intelligence model.

5. The medical-device system of claim 1, wherein the heart failure detector is configured to classify the patient into one of the plurality of phenotypes based on a similarity between the received physiological and clinical information of the patient and one or more of the plurality of phenotypes.

6. The medical-device system of claim 1, wherein the heart failure detector is further configured to:

receive information sensed from the patient by at least one phenotype-specific sensor for the classified phenotype; and confirm or modify the classified phenotype of the patient using the received information sensed by the at least one phenotype-specific sensor.

7. The medical-device system of claim 1, comprising a storage device configured to store a correspondence between the plurality of phenotypes and corresponding candidate heart failure detection settings, wherein to modify the one or more heart failure detection settings, the heart failure detector circuit is configured to select from the stored candidate heart failure detection settings based on the classified phenotype.

8. The medical-device system of claim 1, comprising a sensor circuit configured to selectively sense physiological signal based on the classified phenotype, wherein the heart failure detector circuit is configured to detect the heart failure status using the selectively sensed physiologic signal.

9. The medical-device system of claim 1, wherein to detect the heart failure status in the patient, the heart failure detector circuit is configured to:

compute a composite signal index using the received physiological and clinical information and the modified one or more heart failure detection settings; and detect the heart failure status in response to the composite signal index satisfying a specific condition.

10. The medical-device system of claim 9, wherein the heart failure detector circuit is configured to determine or adjust a detection threshold value based on the classified phenotype, and to detect the heart failure status based on a comparison between the composite signal index and the determined or adjusted detection threshold value.

11. The medical-device system of claim 9, wherein the heart failure detector circuit is configured to:

determine or adjust weights for one or more of a plurality of signal metrics derived from the received physiological and clinical information; and compute the composite signal index using a weighted combination of the plurality of signal metrics.

12. The medical-device system of claim 11, wherein the heart failure detector circuit is configured to determine or adjust the weights for the one or more of the plurality of signal metrics further based on a severity of a symptom or a comorbid condition associated with the classified phenotype.

13. The medical-device system of claim 1, comprising a therapy circuit configured to generate and deliver a heart failure therapy to the patient in accordance with the detected heart failure status.

14. The medical-device system of claim 1, wherein to modify the one or more heart failure detection settings, the heart failure detector circuit is configured to modify a detection threshold value based on the distinct false positive detection rate of the classified phenotype.

15. A method of detecting and managing heart failure in a patient using a medical-device system, the method comprising:

receiving physiological and clinical information of the patient using a receiving circuit of the medical-device system; and by operation of a heart failure detector circuit implemented in the medical-device system, automatically performing operations comprising:

classifying the patient into one of a plurality of phenotypes using the received physiological and clinical information, wherein each phenotype of the plurality of phenotypes is associated with a distinct false positive detection rate for heart failure detection;

modifying one or more heart failure detection settings based on the false positive detection rate of the classified phenotype, the one or more heart failure detection settings including one or more of a detection parameter value or a detection algorithm, wherein the one or more heart failure detection settings are distinct from treatment parameters; and detecting a heart failure status in the patient using the received physiological and clinical information and the modified one or more heart failure detection settings.

16. The method of claim 15, wherein the plurality of phenotypes are each characterized by a cluster of physiological and clinical features in a multi-dimensional feature space including at least one of:

demographic feature;

clinical or laboratory test data feature;

medical history data;

medication information;

heart failure comorbidity information; or sensor signal features produced by one or more ambulatory physiological sensors.

17. The method of claim 15, wherein classifying the patient into one of the plurality of phenotypes is based on a similarity between the received physiological and clinical information of the patient and one or more of the plurality of phenotypes or includes using a trained machine learning (ML) or artificial intelligence model.

18. The method of claim 15, further comprising:

receiving information sensed from the patient by at least one phenotype-specific sensor for the classified phenotype; and confirming or modifying the classified phenotype of the patient using the received information sensed by the at least one phenotype-specific sensor.

19. The method of claim 15, comprising storing a correspondence between the plurality of phenotypes and corresponding candidate heart failure detection settings, wherein modifying the one or more heart failure detection settings includes selecting from the stored candidate heart failure detection settings based on the classified phenotype.

20. The method of claim 15, wherein detecting the heart failure status in the patient includes:

computing a composite signal index using a weighted combination of a plurality of signal metrics derived from the received physiological and clinical information and each scaled by an adjustable weight; and detecting the heart failure status in response to the composite signal index satisfying a specific condition.

* * * * *